(12) United States Patent
Itoh et al.

(10) Patent No.: US 9,200,188 B2
(45) Date of Patent: Dec. 1, 2015

(54) ESTER FOR REFRIGERATOR OILS AND METHOD FOR PRODUCING SAME

(71) Applicant: NOF Corporation, Shibuya-ku, Tokyo (JP)

(72) Inventors: Akio Itoh, Amagasaki (JP); Takeshi Kajiki, Amagasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 14/396,641

(22) PCT Filed: Apr. 25, 2013

(86) PCT No.: PCT/JP2013/062267
§ 371 (c)(1),
(2) Date: Oct. 23, 2014

(87) PCT Pub. No.: WO2013/161960
PCT Pub. Date: Oct. 31, 2013

(65) Prior Publication Data
US 2015/0137025 A1 May 21, 2015

(30) Foreign Application Priority Data
Apr. 26, 2012 (JP) .................................. 2012-100747

(51) Int. Cl.
| | | |
|---|---|---|
| *C07C 67/00* | (2006.01) | |
| *C09K 5/04* | (2006.01) | |
| *C07C 67/08* | (2006.01) | |
| *C10M 105/38* | (2006.01) | |
| *C07C 67/60* | (2006.01) | |
| *C10M 171/00* | (2006.01) | |

(52) U.S. Cl.
CPC .................. *C09K 5/041* (2013.01); *C07C 67/08* (2013.01); *C07C 67/60* (2013.01); *C10M 105/38* (2013.01); *C10M 171/008* (2013.01); *C09K 2205/104* (2013.01); *C09K 2205/134* (2013.01); *C10M 2207/2835* (2013.01); *C10N 2220/028* (2013.01); *C10N 2230/10* (2013.01); *C10N 2240/30* (2013.01)

(58) Field of Classification Search
CPC ........ C07C 67/00; C07C 69/00; C07C 67/58; C07C 67/08; C07C 69/33; C10M 105/00; C10M 105/38; C10N 40/00; C10N 40/30
USPC ............................................. 252/68; 508/569
See application file for complete search history.

(56) References Cited

U.S. PATENT DOCUMENTS

| | | | |
|---|---|---|---|
| 6,774,093 B2 * | 8/2004 | Carr et al. ...................... | 508/485 |
| 2002/0137640 A1 * | 9/2002 | Memita et al. ................ | 508/485 |
| 2010/0190672 A1 * | 7/2010 | Carr et al. ..................... | 508/485 |
| 2014/0097379 A1 * | 4/2014 | Carr ................... | C10M 171/008 252/68 |

FOREIGN PATENT DOCUMENTS

| | | |
|---|---|---|
| JP | 6-145104 A | 5/1994 |
| JP | 8-245504 A | 9/1996 |
| JP | 2002-193882 A | 7/2002 |
| JP | 2007-332134 | 12/2007 |
| JP | 2008-13546 A | 1/2008 |
| WO | WO 02/22548 A1 | 3/2002 |

* cited by examiner

*Primary Examiner* — Douglas Mc Ginty

(74) *Attorney, Agent, or Firm* — Muncy, Geissler, Olds & Lowe, P.C.

(57) ABSTRACT

The present invention relates to an ester for refrigerator oils having less remaining by-products in the ester and having high thermal stability, and a method for producing the ester for refrigerator oils. The ester for refrigerator oils is obtained by treating a crude ester product, which is obtained by reacting a neopentyl polyol having a carbon number of 5 to 10 with an aliphatic carboxylic acid having a carbon number of 4 to 12, with one or more kinds of salts selected from the group consisting of sulfite, bisulfite, and pyrosulfite.

2 Claims, No Drawings

ESTER FOR REFRIGERATOR OILS AND METHOD FOR PRODUCING SAME

BACKGROUND OF THE INVENTION

1. Technical Field

The present invention relates to an ester for refrigerator oils, and a method for producing the same. According to the present invention, it is possible to improve thermal stability of the esters used for refrigerator oils.

2. Background Art

Due to concerns over ozone layer depletion, there has been an attempt to shift from chlorine-containing fluorocarbon refrigerants (chlorine-containing fluorocarbon refrigerants) that have been conventionally used in air-conditioning equipment such as air conditioners, and refrigerators, to fluorocarbon refrigerants containing no chlorine (CFC (chlorofluorocarbon) substitute refrigerants). Lubricants that have been conventionally used as refrigerator oils for chlorine-containing fluorocarbon refrigerants, for example, lubricants with mineral oils or synthetic hydrocarbon oils such as alkylbenzene, have a low compatibility with CFC substitute refrigerants, so that it has become difficult for the conventional lubricants to achieve its full capacity as refrigerator oils due to the shift in refrigerants.

In order to solve the above-noted problem, there has been a study on compounds that show good compatibility with CFC substitute refrigerants. As a result, for example, polyol ester compounds and polyalkylene glycol compounds were found as refrigeration oils, and they have begun to be used instead of conventional refrigerator oils using mineral oils or synthetic hydrocarbon oils.

Among them, a polyol ester is an ester of a neopentyl polyol, such as neopentyl glycol, trimethylol propane, pentaerythritol and dipentaerythritol, and an aliphatic carboxylic acid, and it has been widely used because it has not only an excellent compatibility with CFC substitute refrigerants but also its electrical insulating properties and thermal stability which are suitable for a refrigerator oil.

In recent years, as equipment using the above refrigerator oils has become more compact (use of less refrigerator oil per unit) and saving energy (extension of operation time of a compressor due to inverter control) has been achieved, the working conditions of a refrigerator oil have become more demanding and high quality is required more than ever before for a refrigerator oil. For example, there is a possibility that refrigerator oil is thermally decomposed as it is locally exposed to a high temperature condition with frictional heat at a sliding portion of a compressor, and the generated decomposition product corrodes metal members and causes an adverse effect on the resin material.

Based on the above, refrigerator oil has been required to have a higher thermal stability than ever before.

It is known that the thermal stability of polyol esters relies not only on the chemical structure of polyol esters but also on the production method. Therefore, various methods for obtaining an ester for refrigerator oils having high thermal stability have ever been reported.

For example, Patent Literature 1 discloses a method for simultaneously adding a Lewis acid catalyst and a phosphorus-based reducing agent in an esterification reaction as a production method for obtaining an ester having a high thermal stability.

Also, Patent Literature 2 discloses a method of neutralization with an alkali aqueous solution after adding a hydrocarbon solvent and an alcohol solvent as a method for purifying an ester in the production of an ester having a high thermal stability.

Patent Literature 3 discloses a method for producing an ester for refrigerator oils including a step of adsorbing unreacted carboxylic acid with an inorganic acid-acceptor and then removing the remaining carboxylate in ester by using activated carbon, etc. as a method for producing an ester having excellent stability over a long period.

CITATION LIST

Patent Literature

[Patent Literature 1] Japanese Unexamined Patent Application Publication No. 2002-193882
[Patent Literature 2] International Publication No. WO 2002/022548
[Patent Literature 3] Japanese Unexamined Patent Application Publication No. 2007-332134

SUMMARY OF THE INVENTION

Technical Problem

It is necessary to carry out an esterification reaction at high temperature of e.g., 200° C. or above since a high esterification rate is required in the production of an ester for refrigerator oils. In order to obtain an ester with high thermal stability, it is important to know how the components that are by-products of a high temperature esterification reaction are effectively reduced.

An object of the present invention is to obtain an ester for refrigerator oils with high thermal stability by reducing by-products remaining in the ester.

Solution to Problem

After intensive studies to overcome the above problems, the present inventors have found that an ester with improved thermal stability is obtained by treating a crude ester product obtained by reacting a specific neopentyl polyol with a specific aliphatic carboxylic acid, with specific salts.

That is, the present invention is an ester for refrigerator oils, wherein a crude ester product obtained by reacting a neopentyl polyol having a carbon number of 5 to 10 with an aliphatic carboxylic acid having a carbon number of 4 to 12, is obtained by a treatment with one or more kinds of salts selected from the group consisting of sulfite, bisulfite, and pyrosulfite.

Further, the present invention is the method for producing an ester for refrigerator oils, including steps of, reacting a neopentyl polyol having the carbon number of 5 to 10 with an aliphatic carboxylic acid having the carbon number of 4 to 12 so as to obtain a crude ester product, and treating the resulting crude ester product with one or more kinds of salts selected from the group consisting of sulfite, bisulfite, and pyrosulfite.

Advantageous Effects of the Invention

According to the present invention, an ester for refrigerator oils having high thermal stability can be obtained by reducing by-products remaining in the ester.

DESCRIPTION OF THE EMBODIMENTS (Steps of Creating Crude Ester Product)

A crude ester product is a product that is esterified by reacting a neopentyl polyol having a carbon number of 5 to 10 with an aliphatic carboxylic acid having a carbon number of 4 to 12.

In the present invention, the neopentyl polyol having the carbon number of 5 to 10 is used as an alcohol. The neopentyl polyol is an alcohol having a neopentyl skeleton having no hydrogen atoms in carbon at the β-positions of hydroxyl groups, specifically including neopentyl glycol, 2-n-butyl-2- ethyl-1,3-propanediol, trimethylol ethane, trimethylol propane, pentaerythritol, dipentaerythritol, etc. These alcohols may be used alone or in combination of two or more kinds, respectively.

As the aliphatic carboxylic acids, aliphatic monocarboxylic acids having a linear or branched chain of which the carbon number is 4 to 12 are used. From the viewpoint of the fluorocarbon compatibility and thermal stability of the ester, it is preferable that the carbon number of the aliphatic acid is 5 or more. Further preferably, the carbon number of the aliphatic acid is 10 or less, and particularly preferably 9 or less. Further, from the viewpoint of the fluorocarbon compatibility and thermal stability of ester, it is particularly preferable that the aliphatic acid has a branched chain.

Such aliphatic monocarboxylic acids include, for example, monocarboxylic acids having a linear structure such as valeric acid, pentanoic acid, hexanoic acid, heptanoic acid, octanoic acid, nonanoic acid, decanoic acid, and dodecanoic acid; and monocarboxylic acids having a branched structure, such as 2-methylpropanoic acid, 2-methylbutanoic acid, 2-methylpentanoic acid, 2-ethylbutanoic acid, 2-methylhexanoic acid, 2-ethylpentanoic acid, 2-ethylhexanoic acid, 3,5,5-trimethylhexanoic acid, and neodecanoic acid. The above-noted aliphatic carboxylic acids may be used alone or in combination of two or more kinds, respectively.

It is also possible to use aliphatic dibasic acids together, such as succinic acid, adipic acid, azelaic acid, and sebacic acid. In this case, the proportion of the aliphatic dibasic acid is preferably 30 mass % or less of the total aliphatic acids from the viewpoint of the present invention.

In a preferred embodiment, during an esterification reaction, the alcohol and the aliphatic carboxylic acid are charged so that the molar equivalent of the carboxylic acid groups would be 1.0 to 1.5 relative to the hydroxyl groups of the alcohol, and a dehydration reaction is carried out at 200° C. or above, or preferably at 200° C. to 250° C. It is noted that the dehydration reaction may be performed under an inert gas atmosphere such as nitrogen so as to prevent oxidation degradation of the ester, and under reduced pressure condition so as to efficiently distill produced water. Further, in order to promote the reaction sufficiently and efficiently, a Broenstead acid catalyst or a Lewis acid catalyst may be used.

Subsequently, a step for distilling away the carboxylic acids present in excess in the reaction product under reduced pressure is performed. It is preferable that this step is normally carried out under a reduced pressure degree of 13 kPa or less in the temperature range of 150° C. to 250° C. Further, it is preferable to carry out the step in a stream of an inert gas such as nitrogen so as to prevent the oxidation degradation of the ester as much as possible.

(Treatment Step of the Present Invention)

In the present invention, the crude ester product is treated with one or more kinds of salts selected from the group consisting of sulfite, bisulfite, and pyrosulfite.

The metal atoms constituting the salts used in the present invention include: alkali metals such as sodium and potassium; and alkaline earth metals such as magnesium and calcium. Among these, for the ease of handling as an aqueous solution product and of removal after the treatment, sodium or potassium salts are preferred.

In treating the crude ester product, a method in which a solution of the salts is mixed therewith is preferable. Water may be used as a solvent, and a method in which an aqueous solution containing salts is used, is preferred from the viewpoint of easy handling and treatment effects of the solution.

The concentration of a solution of the salts to be used, particularly an aqueous solution, may be appropriately adjusted depending on the kinds of salts to be used, but it is particularly preferable to use the solution with the concentration of 5 to 35 mass %.

Further, regarding the amount of the solution of salts, particularly an aqueous solution, in treating the crude ester product, it is preferable that 0.1 to 10 parts by mass of the salts in terms of pure content is used relative to 100 parts by mass of the crude ester product. This amount is more preferably 0.2 parts by mass or more, or further preferably 6 parts by mass or less.

In a preferred embodiment, an aqueous solution, in which the concentration in terms of pure content of salts is 0.1 to 10 mass %, is added to the crude ester product, and the mixture is stirred for 0.5 to 3 hours at the temperature range of 30° C. to 95° C. and is allowed to stand still to split into layers under the same temperature condition, followed by discharging the aqueous solution of the lower layer. The time to stand still to split into layers is preferably in the range of 0.5 to 2 hours.

After the treatment with salts, the ester treated with salts may be obtained finally by removing the water remaining in the ester. It is preferable that the water is removed for 0.5 to 2 hours under reduced pressure condition of 13 kPa or less at 50° C. to 100° C. under a nitrogen stream.

(Other Purification Treatments)

Further, it is possible to carry out one or both of the following purification treatment steps (A) and (B) to the crude ester product, in addition to the treatment step with the salts of the present invention.

(A) Neutralization step of neutralizing a remaining acid component originated in the aliphatic carboxylic acid, with an alkaline aqueous solution.
(B) Adsorption step of an adsorption treatment with various adsorbents.

In the neutralization step (A), an alkaline aqueous solution is added to the crude ester product; a remaining acid component originated in the aliphatic carboxylic acid in the ester is neutralized; and washing with water is preferably repeated, and the water is distilled away. As the alkali, potassium hydroxide or sodium hydroxide is preferable.

In the adsorption step (B), after the adsorption treatment is carried out under reduced pressure by adding an adsorbent, the adsorbent is removed by filtration. An adsorbent is preferably alumina (aluminum oxide), magnesia (magnesium oxide), activated clay, activated carbon, acid clay, or zeolite.

When performing both the neutralization step (A) and adsorption step (B), the neutralization step (A) may be carried out before the step (B), or the adsorption step (B) may be performed before the step (A).

Further, the treatment step with salts such as the sulfites of the present invention may be carried out either before or after the neutralization step (A), either before or after the adsorption step (B), or between the neutralization step (A) and the adsorption step (B), to the crude ester product. It is particularly preferable that the treatment step of the present invention is carried out after the neutralization step (A) in terms of effects, and it is particularly preferable to carry out the treatment before the adsorption step (B) in terms of efficiency. It is further preferable that washing with water is repeated after the neutralization with the alkaline aqueous solution and then the treatment of the present invention is performed.

By performing the treatment step of the present invention subsequently to the neutralization step (A) as noted above, it becomes possible to reduce oil-soluble by-products present in the ester without adding complicated steps and by the simple method, thus easily obtaining an ester for refrigerator oils with improved thermal stability.

(Other Additives)

To the ester for refrigerator oils of the present invention, well-known additives, for example, phenol-based antioxidants, metal deactivators such as benzotriazole, thiadiazole, and dithiocarbamate, acid-acceptors such as epoxy compounds or carbodiimide, and phosphorus-based extreme-pressure agents may be appropriately formulated in accordance with a purpose.

(Working Fluid Composition for Refrigerator Oils)

The ester for refrigerator oils of the present invention can also be used as a working fluid composition for refrigerator oils by mixing the ester with a refrigerant. It is possible to use a working fluid composition for refrigerator oils having the mass ratio of an ester for refrigerator oils relative to a refrigerant, for example, from 10:90 to 90:10. The refrigerant used in the working fluid composition includes chlorine-free fluorocarbon refrigerants such as HFC-134a, HFC-125, HFC-32, and HFO-1234yf, and mixed refrigerants such as R-407C and R-410A. The refrigerant used in the working fluid composition can also apply hydrocarbon refrigerants having the carbon number of 1 to 5 and natural refrigerants including carbon dioxide.

EXAMPLES

The present invention will be explained in further detail with examples below.

Described below are analysis methods and a test method for the esters produced in the examples and comparative examples of the present invention.

<Acid Value> Measured according to JIS C-2101.
<Hydroxyl Value> Measured according to JIS K-0070.
<Hue (APHA)> Measured according to JOCS 2.2.1.4-1996.
<Sealed Tube Test> 10 g of a sample (ester) in which its water concentration was adjusted to 200 ppm or less in advance, 5 g of fluorocarbon R-410A, and each of an iron piece, copper piece, and aluminum piece having 1.6 mm in diameter and 50 mm in length were enclosed and sealed in a glass tube. After heating for 14 days at 200° C., the appearance of each metal piece, and the acid value and hue (APHA) of fluorocarbon-containing samples without metal pieces were measured.

Synthesis of Crude Ester Product (Crude Ester Product A)

In a 3 L four-necked flask mounted with a thermometer, a nitrogen inlet tube, and a stirrer as well as a cooling tube and an oil-water separation tube, 395 g of pentaerythritol, 975 g of 2-methyl hexanoic acid and 1030 g of 3,5,5-trimethyl hexanoic acid (carboxylic acid group/hydroxyl group=1.20) were charged, and were reacted at 220° C. and normal pressure and under a stream of nitrogen, while the reaction water was being distilled. The reaction was continued until the hydroxyl value would be 5.0 mgKOH/g or less. Then, the unreacted carboxylic acid was removed over a period of one hour under the reduced pressure of 1 to 5 kPa. The resulting ester was cooled to room temperature, and 1831 g of a crude ester product was obtained.

(Crude Ester Product B)

In a 3 L four-necked flask mounted with a thermometer, a nitrogen inlet tube, and a stirrer as well as a cooling tube and an oil-water separation tube, 316 g of neopentyl glycol, 170 g of pentaerythritol, and 1914 g of 2-ethyl hexanoic acid (carboxylic acid group/hydroxyl group=1.20) were charged, and were reacted at 240° C. and normal pressure and under a stream of nitrogen, while the reaction water was being distilled. The reaction was continued until the hydroxyl value would be 5.0 mgKOH/g or less. Then, the unreacted carboxylic acid was removed over a period of one hour under the reduced pressure of 1 to 5 kPa. The resulting ester was cooled to room temperature, and 1861 g of a crude ester product was obtained.

(Crude Ester Product C)

In a 3 L four-necked flask mounted with a thermometer, a nitrogen inlet tube, and a stirrer as well as a cooling tube and an oil-water separation tube, 507 g of pentaerythritol, 757 g of n-pentanoic acid, 757 g of n-heptane acid, and 379 g of 3,5,5-trimethyl hexanoic acid (carboxylic acid group/hydroxyl group=1.20) were charged, and were heated gradually while paying attention to the reflux amount of the monocarboxylic acids under a stream of nitrogen. The mixture was reacted at 210° C. and normal pressure, while the reaction water was being distilled. The reaction was continued until the hydroxyl value would be 5.0 mgKOH/g or less. Then, the unreacted carboxylic acid was removed over a period of one hour under the reduced pressure of 1 to 5 kPa. The resulting ester was cooled to room temperature, and 1824 g of a crude ester product was obtained.

(Crude Ester product D) In a 3 L four-necked flask mounted with a thermometer, a nitrogen inlet tube, and a stirrer as well as a cooling tube and an oil-water separation tube, 297 g of pentaerythritol, 99 g of dipentaerythritol, 1002 g of 2-ethylhexanoic acid, and 1002 g of 3,5,5-trimethyl hexanoic acid (carboxylic acid group/hydroxyl group=1.20) were charged, and were reacted at 250° C. and normal pressure and under a stream of nitrogen, while the reaction water was distilled. The reaction was continued until the hydroxyl value would be 5.0 mgKOH/g or less. Then, the unreacted carboxylic acid was removed over a period of two hours under the reduced pressure of 1 to 5 kPa. The resulting ester was cooled to room temperature, and 1730 g of a crude ester product was obtained.

Treatment of Purifying Crude Ester Product

Purification treatment was carried out to the crude ester products obtained in the above-noted methods by the following methods, thus providing esters for refrigerator oils.

(Treatment of Purifying Crude Ester Product A: Examples 1, 2 and Comparative Example 1)

200 g of the crude ester product A was heated up to 85° C. To the ester, a 10 mass % potassium hydroxide aqueous solution was added and was stirred for 30 minutes for neutralization treatment (1.5 times as much as alkali equivalent calculated from the acid value of the ester). After being allowed to stand still to split into layers, the lower aqueous layer was discharged. Subsequently, the ester was washed three times with 40 g of deionized water. After it was confirmed that the pH of the waste solution after washing with water was neutral, 40 g of a 25 mass % sodium bisulfite aqueous solution (5 mass % in terms of pure content of sodium bisulfite relative to the crude ester product) was added under the condition of a temperature of 80° C., followed by stirring for 30 minutes. Then, the lower aqueous layer was discharged, and the mixture was stirred and washed with 40 g of deionized water. Subsequently, dehydration was carried out under the condition of 85° C. and 4 kPa, and 1 g of activated clay and of aluminum oxide were added respectively. Then, adsorption treatment was carried out for two hours under the condition of 85° C. and 4 kPa. Finally, filtration was carried out with a 1 micron filter, thus obtaining a purified product of Example 1.

Also, the same treatment as in Example 1 was carried out to the crude ester product A, except that the treatment with 40 g of a 5 mass % sodium bisulfite aqueous solution (1 mass % in terms of pure content of sodium bisulfite relative to the crude ester product) was carried out, thereby obtaining a purified product of Example 2.

Further, the same treatment as in Example 1 was carried out to the crude ester product A, except the treatment with the sodium bisulfite aqueous solution was not carried out, thus obtaining a purified product of Comparative Example 1.

(Treatment of Purifying Crude Ester Product B: Examples 3, 4, 5, and Comparative Example 2)

200 g of the crude ester product B was heated up to 85° C. To the ester, a 10 mass % potassium hydroxide aqueous solution was added and was stirred for 30 minutes for neutralization treatment (1.5 times as much as alkali equivalent calculated from the acid value of the ester). After being allowed to stand still to split into layers, the lower aqueous layer was discharged. Subsequently, the ester was washed three times with 40 g of deionized water. After it was confirmed that the pH of the waste solution after washing with water was neutral, 40 g of a 20 mass % sodium sulfite aqueous solution (4 mass % in terms of pure content of sodium sulfite relative to the crude ester product) was added under the condition of a temperature of 85° C., followed by stirring for 30 minutes. Then, the lower aqueous layer was discharged, and the mixture was stirred and washed with 40 g of deionized water. Subsequently, dehydration was carried out under the condition of 85° C. and 4 kPa, and 1 g of activated clay and of aluminum oxide were added respectively. Then, adsorption treatment was carried out for two hours under the condition of 85° C. and 4 kPa. Finally, filtration was carried out with a 1 micron filter, thus obtaining a purified product of Example 3.

Also, the same treatment as in Example 3 was carried out to the crude ester product B, except that the salt concentration of the sodium sulfite aqueous solution used for the treatment was 10 mass % (2 mass % in terms of pure content of sodium sulfite relative to the crude ester product), thereby obtaining a purified product of Example 4.

Also, the same treatment as in Example 3 was carried out to the crude ester product B, except that 40 g of a 20 mass % potassium bisulfite aqueous solution (4 mass % in terms of pure content of potassium bisulfite relative to the crude ester product) was used for the treatment under the condition of a temperature of 85° C., thereby obtaining a purified product of Example 5.

Further, the same treatment as in Example 3 was carried out to the crude ester product B, except that the treatment with the sodium sulfite aqueous solution was not carried out, thus obtaining a purified product of Comparative Example 2.

(Treatment of Purifying Crude Ester Product C: Examples 6, 7, 8, and Comparative Example 3)

200 g of the crude ester product C was heated up to 85° C. To the ester, a 10 mass % potassium hydroxide aqueous solution was added and was stirred for 30 minutes for neutralization treatment (1.5 times as much as alkali equivalent calculated from the acid value of the ester). After being allowed to stand still to split into layers, the lower aqueous layer was discharged. Subsequently, the ester was washed three times with 40 g of deionized water. After it was confirmed that the pH of the waste solution after washing with water was neutral, 40 g of a 25 mass % sodium pyrosulfite aqueous solution (5 mass % in terms of pure content of sodium pyrosulfite relative to the crude ester product) was added under the condition of a temperature of 85° C., followed by stirring for 30 minutes. Then, the lower aqueous layer was discharged, and the mixture was stirred and washed with 40 g of deionized water. Subsequently, dehydration was carried out under the condition of 85° C. and 4 kPa, and 1 g of activated clay and of aluminum oxide were added respectively. Then, adsorption treatment was carried out for two hours under the condition of 85° C. and 4 kPa. Finally, filtration was carried out with a 1 micron filter, thus obtaining a purified product of Example 6.

Also, the same treatment as in Example 6 was carried out to the crude ester product C, except that the salt concentration of the sodium pyrosulfite aqueous solution used for the treatment was 10 mass % (2 mass % in terms of pure content of sodium pyrosulfite relative to the crude ester product), thereby obtaining a purified product of Example 7.

Further, the same treatment as in Example 6 was carried out to the crude ester product C, except that the salt concentration of the sodium pyrosulfite aqueous solution used for the treatment was 1 mass % (0.2 mass % in terms of pure content of sodium pyrosulfite relative to the crude ester product), thereby obtaining a purified product of Example 8.

Furthermore, the same treatment as in Example 6 was carried out to the crude ester product C, except that the treatment with the sodium pyrosulfite aqueous solution was not carried out, thus obtaining a purified product of Comparative Example 3.

(Treatment of Purifying Crude Ester Product D: Examples 9, 10, and Comparative Example 4)

200 g of the crude ester product D was heated to 85° C. To the ester, a 10 mass % potassium hydroxide aqueous solution was added and was stirred for 30 minutes for neutralization treatment (1.5 times as much as alkali equivalent calculated from the acid value of the ester). After being allowed to stand still to split into layers, the lower aqueous layer was discharged. Subsequently, the ester was washed three times with 40 g of deionized water. After it was confirmed that the pH of the waste solution after washing with water was neutral, 40 g of a 30 mass % potassium sulfite aqueous solution (6 mass % in terms of pure content of potassium sulfite relative to the crude ester product) was added under the condition of a temperature of 85° C., followed by stirring for 30 minutes. Then, the lower aqueous layer was discharged, and the mixture was stirred and washed with 40 g of deionized water. Subsequently, dehydration was carried out under the condition of 85° C. and 4 kPa, and 1 g of activated clay and of aluminum oxide were added respectively. Then, adsorption treatment was carried out for two hours under the condition of 85° C. and 4 kPa. Finally, filtration was carried out with a 1 micron filter, thus obtaining a purified product of Example 9.

Also, the same treatment as in Example 9 was carried out to the crude ester product D, except that 40 g of a 3 mass % potassium sulfite aqueous solution (0.6 mass % in terms of pure content of potassium sulfite relative to the crude ester product) was used, thereby obtaining a purified product of Example 10.

Further, the same treatment as in Example 9 was carried out to the crude ester product D, except that the treatment with the potassium sulfite aqueous solution was not carried out, thus obtaining a purified product of Comparative Example 4.

Evaluation of Thermal Stability with Sealed Tube Test of Esters

Table 1 shows the evaluation results of thermal stability in a sealed tube test on each ester obtained in the above production step.

TABLE 1

| | Crude ester product | | | Treatment conditions with sulfite | | Physical property | | Sealed tube test | | |
|---|---|---|---|---|---|---|---|---|---|---|
| | Alcohol (mass %) | Carboxylic acid (mass %) | Used sulfite | Salt concentration (mass %) | concentration in terms of pure content* (mass %) | Hue (APHA) | Acid value (mgKOH/g) | Appearance of metal | Hue (APHA) | Acid value (mgKOH/g) |
| Ex. 1 | Pentaerythritol (100) | 2-methylhexanoic acid (49) 3,5,5-trimethylhexanoic acid (51) | Sodium bisulfite | 25 | 5 | 30 | <0.01 | No change | 40 | 0.10 |
| Ex. 2 | | | | 5 | 1 | | | No change | 40 | 0.11 |
| Comp. Ex. 1 | | | Untreated | — | — | | | Fe discoloration | 60 | 0.22 |
| Ex. 3 | Neopentylglycol (65) Pentaerythritol (35) | 2-ethylhexanoic acid (100) | Sodium sulfite | 20 | 4 | 20 | <0.01 | No change | 20 | 0.11 |
| Ex. 4 | | | | 10 | 2 | | | No change | 30 | 0.11 |
| Ex. 5 | | | Potassium bisulfite | 20 | 4 | | | No change | 20 | 0.10 |
| Comp. Ex. 2 | | | Untreated | — | — | | | Fe mild discoloration | 40 | 0.18 |
| Ex. 6 | Pentaerythritol (100) | Pentanoic acid (40) Heptanoic acid (40) 3,5,5-trimethylhexanoic acid (20) | Sodium pyrosulfite | 25 | 5 | 30 | <0.01 | No change | 50 | 0.23 |
| Ex. 7 | | | | 10 | 2 | | | No change | 50 | 0.25 |
| Ex. 8 | | | | 1 | 0.2 | | | No change | 60 | 0.30 |
| Comp. Ex. 3 | | | Untreated | — | — | | | Fe discoloration | 70 | 0.42 |
| Ex. 9 | Pentaerythritol (75) Dipentaerythritol (25) | 2-ethylhexanoic acid (50) 3,5,5-trimethylhexanoic acid (50) | Potassium sulfite | 30 | 6 | 40 | <0.01 | No change | 40 | 0.08 |
| Ex. 10 | | | | 3 | 0.6 | | | No change | 40 | 0.11 |
| Comp. Ex. 4 | | | Untreated | — | — | | | Fe mild discoloration | 50 | 0.13 |

*The amount of each sulfite aqueous solution used in the treatment is 40 g relative to 200 g of a crude ester product.

According to the results in Table 1, it may be understood that the esters that were treated with at least one of sulfites selected from sulfite, bisulfite, and pyrosulfite shown in the present invention (Examples 1-10) are effective in preventing corrosion of iron pieces, in comparison with the esters without the treatment (Comparative Examples 1 to 4). Thus, according to the above results, it was shown that the esters for refrigerator oils with improved thermal stability might be obtained by carrying out the present invention.

The invention claimed is:

1. An ester for refrigerator oils, obtained by treating a crude ester product with one or more kinds of salts selected from the group consisting of sulfite, bisulfite, and pyrosulfite at a temperature range of 30° C. to 95° C., wherein the crude ester product is obtained by reacting a neopentyl polyol having a carbon number of 5 to 10 with an aliphatic carboxylic acid having a carbon number of 4 to 12.

2. A method for producing an ester for refrigerator oils, comprising steps of:
   reacting a neopentyl polyol having a carbon number of 5 to 10 with an aliphatic carboxylic acid having a carbon number of 4 to 12 so as to obtain a crude ester product; and
   treating the resulting crude ester product with one or more kinds of salts selected from the group consisting of sulfite, bisulfite, and pyrosulfite at a temperature range of 30° C. to 95° C.

* * * * *